United States Patent [19]

Smith

[11] 4,041,121

[45] * Aug. 9, 1977

[54] METHOD FOR MAKING HIGH FLUID-HOLDING FIBER MASS

[75] Inventor: Frederick R. Smith, Wilmington, Del.

[73] Assignee: Avtex Fibers Inc., Valley Forge, Pa.

[*] Notice: The portion of the term of this patent subsequent to Nov. 11, 1992, has been disclaimed.

[21] Appl. No.: 625,445

[22] Filed: Oct. 24, 1975

Related U.S. Application Data

[63] Continuation-in-part of Ser. No. 309,290, Nov. 24, 1972, abandoned.

[51] Int. Cl.$^2$ .................................................. D01F 2/08
[52] U.S. Cl. ...................................... 264/191; 106/114; 106/168; 128/284; 260/17 R; 264/188

[58] Field of Search .......................... 260/17 R, 17 A; 264/188, 191; 128/284; 106/164, 168, 176

[56] References Cited

U.S. PATENT DOCUMENTS

| | | | |
|---|---|---|---|
| 2,901,457 | 8/1959 | Stoner et al. | 260/17 R |
| 3,377,412 | 4/1968 | Franks | 260/17 R |
| 3,669,103 | 6/1972 | Harper et al. | 128/284 |
| 3,670,731 | 6/1972 | Harmon | 128/284 |
| 3,919,385 | 11/1975 | Smith | 264/184 |
| 3,951,889 | 4/1976 | Smith | 260/17 R |

*Primary Examiner*—Jay H. Woo
*Attorney, Agent, or Firm*—Arthur R. Eglington

[57] ABSTRACT

Method for making alloy fibers having high fluid-holding capacity, the alloy fibers being comprised of a matrix of regenerated cellulose having polyvinylpyrrolidone uniformly dispersed therein.

2 Claims, No Drawings

METHOD FOR MAKING HIGH FLUID-HOLDING FIBER MASS

CROSS-REFERENCE

This application is a continuation-in-part of my application Ser. No. 309,290, filed Nov. 24, 1972, now abandoned and entitled Method for Making High Fluid-Holding Fiber Mass.

The present invention is directed to a method for making alloy fibers having high fluid-holding capacity.

Known in the art are alloy fibers, consisting of sodium carboxymethyl cellulose and regenerated cellulose, which can be employed in various articles which are intended to absorb body liquids. While the fluid-holding capacity of these alloy fibers is greater than that of conventional regenerated cellulose fibers, this advantage is at least partially offset by their higher manufacturing costs.

One mode of making such known alloy fibers involves the mixing of sodium carboxymethyl cellulose into viscose and then converting this mixture into fibers using the conventional viscose spinning system. Drying of the resulting alloy fibers to cardable form is difficult. This objective can be attained, however, by treating the alloy fibers with special finishes, removing water therefrom with alcohol, and then finally drying the alcohol-wet fibers. Aside from introducing greater complexity into the manufacturing process, the finishing and drying of the alloy fibers by solvent exchange is a relatively costly procedure. Accordingly, a primary object is to provide a new or generally improved and more satisfactory method for making absorbent alloy fibers.

Another object is to provide a method for making absorbent alloy fibers of regenerated cellulose containing a uniform dispersion of polyvinylpyrrolidone.

Still another object of this invention is the provision of a method for making absorbent alloy fibers from a mixture of viscose and polyvinylpyrrolidone in which no special finishes and/or drying procedures are required.

As employed throughout the description and claims, the terminology "alloy fibers" refers to cellulose fibers having polyvinylpyrrolidone contained therein. Similarly, "fluid-holding capacity" is a measure of liquid absorbed into the fibers of a mass of alloy fibers, together with the liquid retained within the interstices of such fiber mass.

In accordance with the present invention, high fluid-holding alloy fibers are prepared by mixing an aqueous solution of polyvinylpyrrolidone with a filament-forming viscose, shaping the mixture into fibers, coagulating and regenerating the shaped fibers and thereafter drying the same. Viscose constitutes the major portion of the mixture and the shaped alloy fibers are coagulated and regenerated by known means, and preferably in an acid bath containing sulfuric acid and sodium sulfate. Zinc sulfate is often incorporated in the bath as well as other coagulation modifiers, as desired. No special finishes and/or drying procedures are required to render the alloy fibers in a form which can be carded without difficulty.

The viscose which is employed in making the alloy fibers is, desirably, of a composition as is used in making conventional regenerated cellulose fibers. The composition of such viscose is well documented in the prior art and, in general, is produced by reacting alkali cellulose with carbondisulfide, with the resulting sodium cellulose xanthate being diluted with aqueous caustic to provide the resulting viscose with a desired cellulose and alkali content. Addtitives or modifiers may be mixed in the viscose if desired.

Polyvinylpyrrolidone which is suitable for use in the present invention has an average molecular weight ranging from 100,000 to 400,000 and, more desirably, from 160,000 to 360,000, and a preferred K-valve of from 50 to 100. The procedure for determining the K-valve of such polymers is known in the art, as disclosed in Modern Plastics, 1945, No. 3, starting on Page 157. Polyvinylpyrrolidone of desired character is commercially available, for example, under the designation of K-60 and K-90 from General Aniline and Film Corporation.

In accordance with the present invention the polyvinylpyrrolidone is incorporated directly into a viscose and is employed in relatively large quantities, ranging from about 6% to about 40%, and more desirably from above 20%, based upon the weight of the cellulose in the viscose. Fibers formed from a viscose containing less than about 6% of polyvinylpyrrolidone do not differ appreciably from conventional regenerated cellulose fibers in their fluid-holding capacity. Increasing the amount of polyvinylpyrrolidone in the viscose above the range specified generally results in no improvement and perhaps a slight decrease in the fluid-holding capacity of the alloy fibers which are produced. Thus as indicated in Example I, the use of proportions in the range of 50 to 70% based on cellulose, such as the 65:35 and 60:40 ratios in Samples F and G, gave substantially the same fluid-holding capacity as 45%, based on cellulose; that is, the 70:30 ratio of Sample E.

The polyvinylpyrrolidone described exhibits good solubility in water and, in accordance with the method of the present invention, aqueous solutions of polyvinylpyrrolidone are injected into the viscose as it is pumped to spinnerets for extrusion. Alternately, aqueous solutions of polyvinylpyrrolidone and viscose may be passed through a blender or homogenizer if it is necessary to secure a more uniform dispersion. After the spinning, coagulation, and regeneration stages, the shaped continuous tow of filaments undergoes the usual processing, which may include stretching if desired, and is then dried by conventional means. Generally, before drying, the continuous tow of filaments is cut into staple of a desired length. In general the resulting alloy fibers experience no bonding during drying and can be subsequently carded with no difficulty by the manufacturer of articles incorporating such fibers.

The alloy fibers made by the method of the present invention are adapted for use in a variety of articles, such as sanitary napkins and tampons, in which high fluid retention is an essential characteristic. In the manufacture of such articles, the alloy fibers necessitate no special techniques or equipment and they may be blended with other fibers which may or may not enhance the absorbent properties of the resulting articles. Fibers with which the alloy fibers may be blended include, for example, rayon, cotton, chemically modified rayon or cotton, cellulose acetate, nylon, polyester, acrylic, polyolefin, etc.

EXAMPLE I

Using conventional rayon spinning equipment, aqueous solutions of polyvinylpyrrolidone, designated as K-60 (GAF Corporation) and having an average molecular weight of about 160,000 and K-valve of 50–62, were separately injected by a metering pump into a viscose stream during its passage through a blender and the blend thereafter extruded. During this the blend was subjected to high mechanical shearing. The viscose composition was 9.0% cellulose, 6.0% sodium hydroxide and 32% (based upon the weight of the cellulose) carbon disulfide. The viscose ball fall was 56 and its common salt test was 7.

The mixtures of viscose and polyvinylpyrrolidone were extruded through a 720 hole spinneret into an aqueous spinning bath consisting of 7.5% by weight of sulfuric acid, 18% by weight of sodium sulfate, and 3.5% by weight of zinc sulfate. After passage through the spinning bath, the resulting continuous tow was washed with water, desulfurized with an aqueous solution of sodium hydrosulfide, washed with water, acidified with an aqueous HCl solution, and again washed with water. The still wet multifilament tow was cut into staple fibers and, without any further treatment, dried.

The fluid-holding capacity of sample fibers, made with various approximate proportions (tabulated below) of cellulose and polyvinylpyrrolidone in the spinning solution, was determined using the following test procedure.

Sample staple fibers were carded or otherwise well opened and then conditioned at 75° F and 58% relative humidity. Two grams of such alloy fibers were placed in a one-inch diameter die, pressed to a thickness of 0.127 inch, and maintained in this condition for one minute. This compressed pellet of fibers was removed from the die and placed on a porous plate of a Buchner funnel. The upper surface of the pellet was then engaged with a plunger which was mounted for free vertical movement, the plunger having a diameter of one inch and a weight of 2.4 pounds.

The funnel stem was connected by a flexible hose to a dropping bottle from which water was introduced into the funnel to wet the pellet of fibers. Control over the water flow was exercised by the position of the dropping bottle. After an immersion period of two minutes, the water was permitted to drain from the fiber pellet for 3 minutes, after which the still wet pellet was removed from the funnel and weighed. One-half of the weight of water in the sample pellet is a measure of the fluid-holding capacity of the fibers, expressed in cc/g.

The test results of sample fibers, as described above, are set forth in Table I.

EXAMPLE II

A 20% aqueous solution of polyvinylpyrrolidone, designated as K-90 (GAF Corporation) and having an average molecular weight of 360,000 and a K-value of 80–100, was injected into a viscose having a composition as described in Example I, after which the mixture was extruded as a continuous tow and processed as described above. The relative proportions of cellulose and polyvinylpyrrolidone in the spinning solution were 83:17. The resulting fibers had a fluid-holding capacity (tested as in Ex. I) which was 28% higher than conventional regenerated cellulose fibers.

EXAMPLE III

Aqueous solutions of polyvinylpyrrolidone, designated as K-90 (GAF Corporation) and having an average molecular weight of about 160,000 and K-value of 80–100, were separately injected into a viscose having a composition as described in Example I. In a manner as described in Example I, the mixtures of viscose and polyvinylpyrrolidone shaped into a tow, treated with an aqueous solution containing 1.0% Span 20 and then cut into staple fibers.

Two and one-half grams of the different fibers prepared as described above were separately made into tampons by the following procedure: The fibers were carded into webs, each having a length of about 6 inches and being of variable thickness and width. Each of these webs was individually rolled in the direction of its width to provide a six inch roll and a string was looped about the center thereof. Each such roll was then folded on itself at the string loop and drawn into a 1/2 inch tube within which it was compressed by a clamp and plunger. After compression, the resulting tampons were removed, allowed to stand for a period of about 30 minutes during which the tampons recovered to a bulk density of about 0.4 g/cc. and were then evaluated for their capacity to hold water by the Syngyna Method, as described by G.W. Rapp in a June 1958 publication of the Department of Research, Loyola University, Chicago, Ill. The results of such test are set forth in Table II for fibers made with various approximate proportions (as tabulated in Table II) of cellulose and polyvinylpyrrolidone in the spinning solution.

It is to be understood that changes and variations may be made without departing from the spirit and scope of the invention as defined in the appended claims.

TABLE I

| Sample | Cellulose | Polyvinyl-Pyrrolidone | Fluid-holding Capacity cc/g | % Water Retention |
|---|---|---|---|---|
| A | 100 | 0 | 3.06 | 105 |
| B | 95 | 5 | 3.16 | 112 |
| C | 90 | 10 | 3.52 | 121 |
| D | 80 | 20 | 4.15 | 145 |
| E | 70 | 30 | 4.69 | 186 |
| F | 65 | 35 | 4.68 | 178 |
| G | 60 | 40 | 4.65 | 190 |

% Water Retention is the percent water retained by the loose mass of fibers after centrifuging the same at 1G for 3.5 minutes.

TABLE II

| Sample | Cellulose | Polyvinyl-Pyrrolidone | Fluid-holding Capacity cc/g |
|---|---|---|---|
| J | 100 | 0 | 4.36 |
| K | 90 | 10 | 4.84 |
| L | 85 | 15 | 5.38 |
| M | 80 | 20 | 5.46 |
| N | 75 | 25 | 5.65 |

I claim:

1. A method of making fluid absorbent alloy fibers comprising mixing an aqueous solution of polyvinylpyrrolidone with a filament-forming viscose, said polyvinylpyrrolidone have an average molecular weight of from about 100,000 and 400,000 and a K-value of from 50 to 100 and being present in an amount less than, but at least 6% of, the weight of the cellulose in the viscose, shaping the mixture into fibers, coagulating and regenerating the shaped fibers of regenerated cellulose containing said polyvinylpyrrolidone dispersed therein, and thereafter drying the fibers, said shaping, coagulating and regenerating being effected by extruding the viscose mixture through a spinnerette into a spinning bath comprising sulfuric acid, sodium sulfate and zinc sulfate, said polyvinylpyrrolidone being present in amount such as to increase the water-holding capacity of said fibers.

2. A method as defined in claim 1 wherein the polyvinylpyrrolidone is present in an amount of at least 20% based on the weight of the cellulose.

* * * * *